United States Patent
Stuker et al.

(10) Patent No.: US 9,746,419 B2
(45) Date of Patent: Aug. 29, 2017

(54) OPTICAL MRI DEVICE

(75) Inventors: Florian Stuker, Zurich (CH); Katerina Dikaiou, Neo Faliro Piraeus (GR); Christof Baltes, Son (NL); Markus Rudin, Eglisau (CH)

(73) Assignee: University of Zurich, Zurich (CH)

( * ) Notice: Subject to any disclaimer, the term of this patent is extended or adjusted under 35 U.S.C. 154(b) by 732 days.

(21) Appl. No.: 12/662,815

(22) Filed: May 5, 2010

(65) Prior Publication Data
US 2010/0292563 A1    Nov. 18, 2010

(30) Foreign Application Priority Data
May 12, 2009   (EP) .................................... 09160047

(51) Int. Cl.
*A61B 5/05* (2006.01)
*G01N 21/64* (2006.01)
(Continued)

(52) U.S. Cl.
CPC ....... *G01N 21/6456* (2013.01); *A61B 5/0035* (2013.01); *A61B 5/0073* (2013.01);
(Continued)

(58) Field of Classification Search
USPC .............. 600/407, 409–10, 476, 411, 312; 382/128, 131
See application file for complete search history.

(56) References Cited

U.S. PATENT DOCUMENTS

| 5,750,989 | A  | * | 5/1998 | Lindsay et al. ............... 850/14 |
| 2004/0015062 | A1 | * | 1/2004 | Ntziachristos et al. ...... 600/312 |
| 2007/0274580 | A1 | * | 11/2007 | Ntziachristos et al. ...... 382/131 |

OTHER PUBLICATIONS

Ciprian Catana et al., "Simultaneous acquisition of multislice PET and MR images: Initial results with MR-compatible PET scanner", The Journal of Nuclear Medicine, 47(12):1968-1976, Dec. 2006.
(Continued)

*Primary Examiner* — Joel F Brutus
(74) *Attorney, Agent, or Firm* — Paul Vincent (57) ABSTRACT

A dual modality imaging apparatus, comprising a magnetic resonance imaging (=MRI) system and a fluorescence molecular tomography (=FMT) system, for investigating a sample (42) located at a sample position (10), wherein the MRI system comprises a magnet (9) with a room temperature bore (8), with the sample position (10) located within the bore (8), and wherein the FMT system comprises means for directing a light beam (12, 17; 30) towards the sample position (10), and a position-sensitive detector (37) for collecting fluorescence light from the sample (42), is characterized in that the position-sensitive detector (37) is located within the bore (8), wherein at least part of the sample (42) is imaged onto the position-sensitive detector (37), and that the means for directing the light beam (12, 17; 30) comprise a focusing device for focusing the light beam (12, 17; 30) into a focal spot (41) on the sample (42), and a scanning device for scanning the focal spot (41) on the sample (42). The apparatus is simple in design and versatile in application, and in particular imposes less limitations on the maximum number of source/detector pairs during FMT imaging, thus allowing a better FMT image resolution.

15 Claims, 5 Drawing Sheets

(51) Int. Cl.
*A61B 5/00* (2006.01)
*G01N 21/47* (2006.01)

(52) U.S. Cl.
CPC ....... *A61B 5/0077* (2013.01); *G01N 21/4795* (2013.01); *A61B 5/0042* (2013.01); *A61B 2503/40* (2013.01)

(56) References Cited

OTHER PUBLICATIONS

Bernd J. Pichler et al., "Performance test of an LSO-APD detector in a 7-T MRI scanner for simultaneous PET/MRI", Journal of Nuclear Medicine, 47:639-647, 2005.

Edward E. Graves et al., "A submilimeter resolution fluorescence molecular imaging system for small animal imaging", Medical Physics, 30(5):901-911, May 2003.

Vasilis Ntziachristos et al., "Visualization of antitumor treatment by means of fluorescence molecular tomography with annexinV-Cy5.5 conjugate", PNAS, 101(33):12294-12299, Aug. 2004.

Murat Guven et al., "Diffuse optical tomography with a priori anatomical information", Physics in Medicine and Biology, 50:2837-2857, Feb. 2005.

Murat Guven, et al., "Fluorescence optical tomography with a priori information", Multimodal Biomedical Imaging II, edited by Fred S. Azar Proc. of SPIE vol. 6431, 643107, (2007).

Damon Hyde et al., "Hybrid FMT-CT imaging of amyloid-_ plaques in a murine Alzheimer's disease model", Neuroimage, 1:8-9, 2008.

Mark Niedre et al., "Elucidating Structure and Function In Vivo With Hybrid Fluorescence and Magnetic Resonance Imaging", Proceedings of the IEEE/vol. 96, No. 3, 382, Mar. 2008.

Mathieu Allard et al., "Combined magnetic resonance and bioluminescence imaging of live mice", Journal of Biomedical Optics,12(3):034018-1-11, May/Jun. 2007.

Sean Merritt et al., "Coregistration of diffuse optical spectroscopy and magnetic resonance imaging in a rat tumor model", Applied Optics, 42(16):2951-2959, Jun. 2003.

David J. Cuccia et al., "In vivo quantification of optical contrast agent dynamics in rat tumors by use of optical spectroscopy with magnetic resonance imaging coregistration", Applied Optics, 42(16):2940-2950, Jun. 2003.

Heng Xu et al., "Magentic-resonance-imaging-coupled broadband near-infrared tomography system for small animal brain studies", Applied Optics, 44(11):2177-2188, Apr. 2005.

J. Masciotti et al., "Combined optical tomographic and magnetic resonance imaging of tumor bearing mice", Proc. of SPIE vol. 5693, 74,(SPIE, Bellingham, WA, 2005).

Vasilis Ntziachristos et al., "Experimental three-dimensional fluorescence reconstruction of diffuse media by use of a normalized born approximation", Optics Letters, 26(12):893-895, Jun. 2001.

S.Davis et al., "MRI-coupled spectrally resolved fluorescence tomography for in vivo imaging", Proceedings of SPIE—The International Society for Optical Engineering—Multimodal Biomedical Imaging III, Jan. 19, 2008.

V.Ntziachristos et al., "Fluorescent Protein Tomography Scanner for Small Animal Imaging", IEEE Transactions on Medical Imaging, IEEE Service Center, Piscataway, NJ, US, vol. 24, No. 7, Jul. 1, 2005.

S.D.Davis, et al., "Magnetic resonance-coupled fluorescence tomography scanner for molecular imaging of tissue", Review of Scientific Instruments, AIP, Melville, NY, US, vol. 79, No. 6, Jun. 6, 2008.

Lu Zhou et al., "Fluorescence molecular tomography reconstruction with a priori anatomical information". Proceedings of SPIE—Small Animal Whole Body Optical Imaging Based on Genentically Engineered Probes, Jan. 21, 2008.

S.C.Davis et al., "MRI-guided fluorescence tomography of the breast: a phantom study", Proceedings of SPIE—The International Society for Optical Engineering—Multimodal Biomedical Imaging IV, Jan. 24, 2009.

D.S.Kepshire et al., "Subsurface Diffuse Optical Tomography can Localize Absorber and Fluorescent Objects but Recovered Image Sensitivity is Nonlinear with Depth", Applied Optics, OSA, Optical Society of America, Washington, DC, vol. 46, No. 10, Apr. 1, 2007.

* cited by examiner

OPTICAL MRI DEVICE

This application claims Paris Convention priority to EP 09 160 047.8 filed on May 12, 2009 the entire disclosure of which is hereby incorporated by reference.

BACKGROUND OF THE INVENTION

The invention relates to a dual modality imaging apparatus, comprising a magnetic resonance imaging (=MRI) system and a fluorescence molecular tomography (=FMT) system, for investigating a sample located at a sample position, wherein the MRI system comprises a magnet with a room temperature bore, with the sample position located within the bore, and wherein the FMT system comprises means for directing a light beam towards the sample position, and a position-sensitive detector for collecting fluorescence light from the sample.

Such a device is known from Heng Xu et al., Applied Optics Vol. 44, No. 11 (2005), p. 2177-2188, see Ref. [12].

The combination of structural with functional and/or molecular imaging readouts enable proper allocation of functional or molecular information to tissue/organ structures and thereby the establishment (registration) of structure-function relationships. Clinically established examples are the combination of structural and functional Magnetic Resonance Imaging (MRI), where brain areas activated by a specific task are superimposed on high-resolution anatomical images, or the combination x-ray computer tomography (CT)/positron-emission tomography (PET) allowing locating areas of altered metabolic activity with regard to the overall anatomy. MRI/PET scanners are currently under evaluation both as clinical and preclinical imaging devices [1, 2].

The latter approaches using MRI as structural imaging method are attractive because i) MRI provides anatomical information of excellent soft-tissue contrast as its signal intensities are governed by several tissue-specific parameters, and ii) many MRI approaches yield functional/physiological information in addition. A limitation of PET as molecular imaging modality is the short half-life of positron emitting isotopes.

Small animal imaging fluorescence tomography has emerged as an alternative, in particular when using fluorophores absorbing and emitting in the far red or near-infrared range of the electromagnetic spectrum. Fluorescent markers are in general stable. Moreover, the fluorescent properties of a molecule depend on its environment, and therefore can be modulated through molecular interactions allowing the design of smart imaging probes that increase the sensitivity and selectivity of the imaging approach.

The inherent problem when using fluorescent imaging techniques in life animals is photon propagation in a highly scattering and absorbing medium such as tissue. Photons are transported as a diffusive wave rendering the extraction of geometrical information difficult. Yet, recent progress in modeling photon propagation in tissue allows for macroscopic imaging of whole animals (such as mice), the method being called fluorescence molecular tomography (FMT) [3].

Physical limitations of FMT with regard to spatial resolution and depth of light penetration into tissue due to absorption and scattering are compensated by the high sensitivity of the approach that might be used to derive specific information on molecular events which has been demonstrated in tumor models [4]. FMT can detect fluorophores at picomolar concentration and in contrast to PET allows multiplexing, i.e. the parallel detection of several fluorescent reporters with different emission wavelengths. Structural information can be used as a priori knowledge in image reconstruction improving the quality of diffuse optical tomography [5] and fluorescence molecular tomography [6]. Significant efforts are currently ongoing, combining FMT methods with x-ray CT as anatomical imaging modality [7].

In view of the strengths of the two modalities, combining MRI and FMT represents an attractive concept for small animal imaging. A recent publication by Niedre et al. [8] discusses recent developments in fluorescence-MR hybrid imaging, covering aspects of instrument design and development of dual-modality reporter probes. From the instrumentation point of view two strategies can be pursuit:

i) A fully integrated solution with the optical measurement taking place within the magnet. Both measurements are inherently co-registered and can be performed simultaneously under identical physiological conditions.

ii) The second approach uses an animal support compatible for both fluorescence and MR imaging [9]. In this case measurements are taken sequentially on dedicated systems. Assuming proper geometrical calibration of the two imaging modalities, image registration can be achieved by rigid body transformation.

Integrated fluorescence/MR imaging systems described to date use optical fibers that are brought into contact with the sample to guide light in and out of the magnet. They have been applied for diffuse optical spectroscopy measurements in subcutaneous tumors [10, 11]. A similar setup has been used by Heng et al. [12]: Their system for near-infrared tomography of rat brain uses a fiber bundle for light guiding in direct contact with the scalp.

Fiber based systems are inherently limited by a relative small number of source-detector pairs, preventing accurate spatial resolution as the maximum number of voxels that can be reconstructed is $N_S * N_D$, where $N_S$ and $N_D$ are the number of sources and detectors, respectively. In addition, the bulky fiber bundles have substantial space requirements, which may not be compatible with the small magnet bores commonly used in small animal MRI [13].

It is the object of the invention to provide a dual mode imaging apparatus which is simple in design and versatile in application, and in particular imposes less limitations on the maximum number of source/detector pairs during FMT imaging, thus allowing a better FMT image resolution.

SUMMARY OF THE INVENTION

This object is achieved, in accordance with the invention, by a dual mode imaging apparatus as introduced in the beginning, characterized in that the position-sensitive detector is located within the bore, wherein at least part of the sample is imaged onto the position-sensitive detector, and that the means for directing the light beam comprise a focusing device for focusing the light beam into a focal spot on the sample, and a scanning device for scanning the focal spot on the sample.

The present invention proposes to use a light beam, which is focused by a focusing device (e.g. comprising a lens) on the sample surface into a focal spot for fluorescence excitation. This illumination of the sample surface is contact-free, i.e. the light beam travels freely in an area adjacent to the illuminated sample surface.

Further, by means of a scanning device, the focal spot may be moved continuously on the sample surface, in accordance with the invention. Moving the focal spot relative to the sample surface will not damage the sample, in contrast to moving a fiber which is in contact with the sample surface or already putting fibers of a fiber bundle in contact with the sample surface. For measurement purposes, the scanning device directs the focal spot sequentially to different positions on a point grid, wherein the focal spot stays at each of the positions for some time during which the position sensitive detector registers fluorescence light from the sample in its field of view.

With the scanning device, an arbitrary number of positions on the sample surface may be illuminated, as desired by the user for the FMT measurement. These different positions correspond to a number of sources $N_S$, which contributes to the maximum number of voxels $N_S*N_D$ to be reconstructed. Since $N_S$ is basically unlimited in the inventive apparatus, the number of voxels can to easily be altered (in particular increased). For altering (in particular adding) positions on the point grid of focal spots on the sample, no change in the apparatus hardware is necessary.

Since the focal spot is scanned with the scanning means, there is no need for a bundle of fiber optic cables each guiding a light beam to a separate position on the sample surface. The light beam may originate, in accordance with the invention, from a single light source (typically a laser), which can illuminate all positions on the point grid.

Further, according to the invention, the position sensitive detector is placed within the room temperature bore of the magnet, in the vicinity of the sample. The sample surface is imaged onto the detector. Typically, for this purpose, there is one or a plurality of lenses, and apart therefrom, the fluorescence light travels freely from the sample to the detector. There is no need to transfer fluorescence light from the sample to the outside of the bore, and in particular there is no need for a bundle of optical fibers for guiding light from different areas of the sample to the outside of the bore. Thus the overall amount of equipment within the bore can be reduced as compared to the state of the art.

The invention does without direct contact of the sample to optical equipment, which accelerates sample preparation significantly, and also increases the comparability of different measurements.

In a preferred embodiment of the inventive apparatus, the scanning device is located outside the bore. In this way the amount of equipment within the bore can be reduced, leaving more space for, in particular, the sample, the position sensitive detector, and the MRI equipment. Typically, when the scanning device is located outside the bore, there is a mirror located within the bore, which reflects the incoming light beam onto the sample, and the scanning device changes the position or direction of the incoming light beam relative to said mirror.

In an advantageous further development of this embodiment, the FMT system comprises a rigid linkage connecting the scanning device with a sample platform for supporting the sample at the sample position. In this way, the location of the scanning device relative to the sample can be fixed with high accuracy, simplifying the alignment of the incoming light beam.

In an advancement of said further development, the FMT system comprises a guiding and/or a stop located within the bore for inserting and positioning the rigid linkage. The guiding and/or stop can warrant proper alignment of the scanning device and the position-sensitive detector. More generally speaking, the guiding and stop simplify the alignment of equipment affixed within the magnet or the bore (such as gradient coils, or the detector) and equipment affixed to the rigid linkage (such as the scanning device).

Note that the guiding and/or stop may interact with the rigid linkage directly, or with equipment attached to the rigid linkage (such as the sample platform, or a flange attached to the sample platform or the rigid linkage), in accordance with the invention.

In another further development of the above embodiment, the rigid linkage comprises a rigid tube surrounding a part of the light beam. The tube protects the path of the light beam, and in particular prevents its unintended blocking by an object or a user. Further, the tube may help to avoid scattering light within the bore. The tube provides mechanical stability for the coupled scanning device, so the tube has a double function.

A preferred embodiment is characterized in that the scanning device is adapted to move an optical element into different positions, corresponding to different positions of the focal spot of the light beam on the sample, wherein the optical element directs, in particular reflects or guides, the light beam. In this way, continuous movement of an optical element, which is easy to establish and to control, can be transformed in a continuous scanning of the focal spot on the sample, in order to arrive at arbitrary point grid positions chosen by the user (or the software programmed by the user). The optical element is typically a mirror or a lens, which can be rotated and/or linearly shifted, for example by an electric motor and/or a piezo-electric actuator. The optic element typically has two drivable degrees of freedom, or the scanning device comprises two optical elements in series, each with one drivable degree of freedom. The overall two degrees of freedom offered by the scanning device allow the scanning of the two-dimensional point grid on the sample surface.

In a further development of said embodiment, the scanning device comprises
  a scan head and/or
  one or more galvanometric driven mirrors and/or
  an xy stage carrying an optical fiber guiding the light beam, wherein the fiber output of the optical fiber is imaged on the sample. These options are simple to realize in practice.

A preferred embodiment provides that the FMT system comprises
  a laser or
  a white light source with a filter
as a source for the light beam. A laser can provide a light beam of high intensity. The white light source is inexpensive and may, by changing the filter, provide light of different wavelengths, as desired or needed for the sample.

In a highly preferred embodiment, the FMT system comprises a pinhole, which is imaged by the focusing device via the scanning device onto the sample to form the focal spot. This provides a small focal spot size with a simple design.

A further development of this embodiment provides that the focusing device comprises a lens with a focal length of f, and that the optical distance of the pinhole and the lens as well as the optical distance of the lens and the focal spot on the sample is 2*f. In this setup, the lens can be placed outside the bore, since the 2*f distance is typically enough to reach the sample surface within the bore. Thus bulky focusing equipment within the bore can be avoided.

Further, a preferred embodiment of the inventive apparatus is characterized in that the scanning device is arranged for scanning the focal spot on the side of the sample facing the position sensitive detector (=reflection mode arrangement), or that the scanning device is arranged for scanning the focal spot on the side of the sample opposite of the position sensitive detector (=transmission mode arrangement). The reflection mode arrangement is particularly suited for measuring structures close to the sample surface and requires space for equipment only on one side of the sample. The transmission mode arrangement may provide more accurate information on structures located deep inside a sample.

In another advantageous embodiment, the FMT system comprises a plurality of mirrors between a source for the light beam and the scanning device. These mirrors allow a compact design; in particular there may be sections of the light beam which run basically in parallel to each other. Typically, the focusing device is located outside the bore near the bore opening, and the imaging optics require to provide an optical path outside the bore which corresponds to the depth of the bore. This setup then helps to keep the size of the apparatus outside the bore small.

Particularly preferred is en embodiment wherein the MRI system comprises a radio frequency (=RF) coil with a window facing the position-sensitive detector, in particular wherein the RF coil is of surface coil type, or of a saddle coil type, or of bird cage resonator type, or of Alderman-Grant resonator type. The sample surface may be imaged onto the detector through the window, what allows a large field of view on the sample surface, while at the same time the RF coil can be placed near the sample, which is located within the RF coil. Note that the objects to be investigated (such as a mouse or a rat) may only be partially inside the RF coil (such as only with their head) in case only part of the object is of interest.

In a further embodiment, the FMT system comprises a filter device located in front of the position-sensitive detector, preferably wherein the filter device comprises a plurality of selectable or interchangeable filter elements, in particular wherein a plurality of filter elements is arranged on a filter wheel. The filter selects a part of the fluorescence light emitted from the sample to access the detector, in order to obtain specific information from a particular source (such as a particular substance distributed within the sample). For this purpose, the filter is arranged between the sample and the detector. The filter wheel may be rotated to select one of the filter elements. The filter elements are typically of band pass type, with different passing frequencies.

Preferred is also an embodiment wherein the MRI system is of small animal system type or human whole body system type. In a small animal system, animals up to the size of mice and rats may be investigated. In a human whole body system, an adult human being of typical size may be investigated. These MRI system types are of particular interest in science and medicine.

In another preferred embodiment, the position-sensitive detector is an array detector, in particular of Single Photon Avalanche Diode (=SPAD) array type or Charge Coupled Device (=CCD) array type or of CMOS array type. The array detector allows a simultaneous readout of all detector elements contained and thus a fast collection of information. The mentioned specific detector types have shown good results in practice for FMT.

In another embodiment, the position sensitive detector and its electrical connections are shielded against the RF and gradient components of the MRI system. This minimizes noise and interferences within the detector signal and the MRI data, in particular when measuring FMT and MRI simultaneously. However, the inventors noticed that there are detectors, in particular SPAD type detectors, which may be operated within the magnet bore without a shielding at with good quality signal detection.

Further preferred is an embodiment wherein the apparatus is adapted for simultaneous measurement of MRI data and FMT data. In other words, MRI data and FMT data are acquired at the same time. This makes measurements much quicker, and gives a better correlation of the MRI data and the FMT data.

Also within the scope of the present invention is the use of an inventive apparatus wherein MRI data and FMT data are recorded simultaneously. This again makes measurements much quicker, and gives a better correlation of the MRI data and the FMT data.

It should be noted that the magnet of the apparatus may be a superconducting magnet or a permanent magnet, in accordance with the invention.

The inventive apparatus can be used, in particular, for investigating the brain of a small animal, in particular a living small animal. The small animal is typically a mouse, a rat or another mammal or rodent of comparable size. The small animal is preferably unhurt (in particular it is preferred not to remove part of the cranial bone, and not to remove skin from the skull), but the small animal is typically shaved in order to remove fur from the area to be scanned with the focal spot. However, other applications are also possible, in accordance with the invention.

Further advantages can be extracted from the description and the enclosed drawing. The features mentioned above and below can be used in accordance with the invention either individually or collectively in any combination. The embodiments mentioned are not to be understood as exhaustive enumeration but rather have exemplary character for the description of the invention.

The invention is shown in the drawing.

DESCRIPTION OF THE PREFERRED EMBODIMENT

Overview

The present invention relates to the light illumination and detection principles in dual-modality imaging systems combining fluorescence molecular tomography (FMT) and magnetic resonance imaging (MRI).

The design of known fluorescence imaging-MRI hybrid systems, compare e.g. Ref. [12] and [13], is dictated by the use of detectors located outside of the magnet requiring fibers for illumination and fluorescence detection that are in close proximity or even contact to the sample.

The present invention describes a fundamentally different approach of a non-contact FMT setup designed to fit into the bore of a magnetic resonance imaging system, in particular a small animal imaging system, avoiding the restrictions due to the limited number of sources and detection fibers. In the preferred embodiment, a single photon avalanche diode (SPAD) array detector is placed inside the magnet near to the sample. Illumination is provided with a free-space laser beam from outside the magnet that is focused on the sample surface and that can be scanned across an area of interest. The number of sources $N_S$ can be chosen arbitrarily, while the number of detectors $N_D$ is given by the array dimension of the detector. This allows to significantly increase the number of source-detector combination and thereby the image quality.

Aspects of the Invention

In one aspect of the present invention, a device for providing optical tomography and anatomical MR information is provided. The apparatus includes a sample platform for optical and anatomical imaging inside an MR system.

In a further aspect of the present invention, a method of guiding light, scanning a point source and detecting an optical signal in an MR system is provided. The method includes a combination of a scanning part with a signal detection part within one single apparatus.

In another aspect of the present invention, the sample platform is not only constructed for animal brain imaging but can also be adapted to image any part of the present subject. The optical illumination and signal detection works without any contact of the detection and illumination part with the sample.

In yet another aspect of the present invention, the scanning of the beam takes place outside the high magnetic field of the MR system, whereas the detection part is placed in the MR system.

Description of an Embodiment of the Inventive Apparatus

Figure 1:
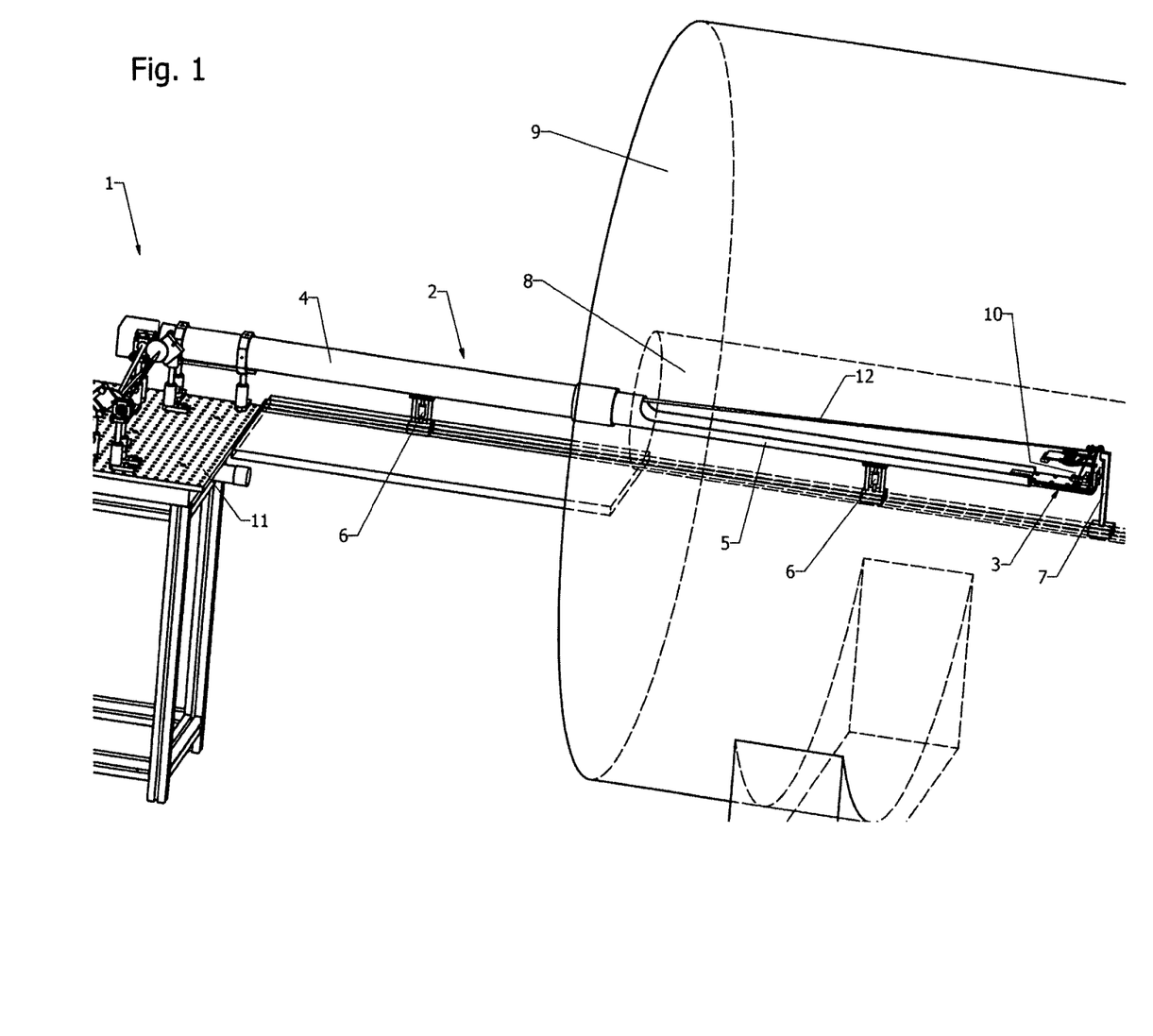
FIG. 1 shows schematically the general setup of an embodiment of an inventive apparatus.

The figures show an embodiment of the inventive apparatus in more detail. The apparatus setup (with FIG. 1 giving an overview) comprises two major parts:

a) An illumination part 1 (compare FIG. 2) aligned on a bread board 11 outside a magnet 9 to ensure the accurate function of a delicate scan head, and b) A second part representing the sample platform 3 (compare FIG. 4), comprising an optical detector and a radio frequency (RF) coil for the magnetic resonance signal detection, placed at the sample position 10 in the isocenter of an MRI system.

To ensure a correct alignment of the illumination part 1 and the sample platform 3, they are linked with two joint tempered glass tubes 4, 5 acting as a rigid linkage 2, with the glass tube 4 outside a room temperature bore 8 of the (here superconducting) magnet 9, and the glass tube 5 mostly located inside the bore 8 being cut open on its upper side. Note that other types of rigid linkage, e.g. of framework type, are also possible. The sample platform 3 is properly positioned within the bore 8 by means of a guiding 6 and a stop 7.

Figure 2:
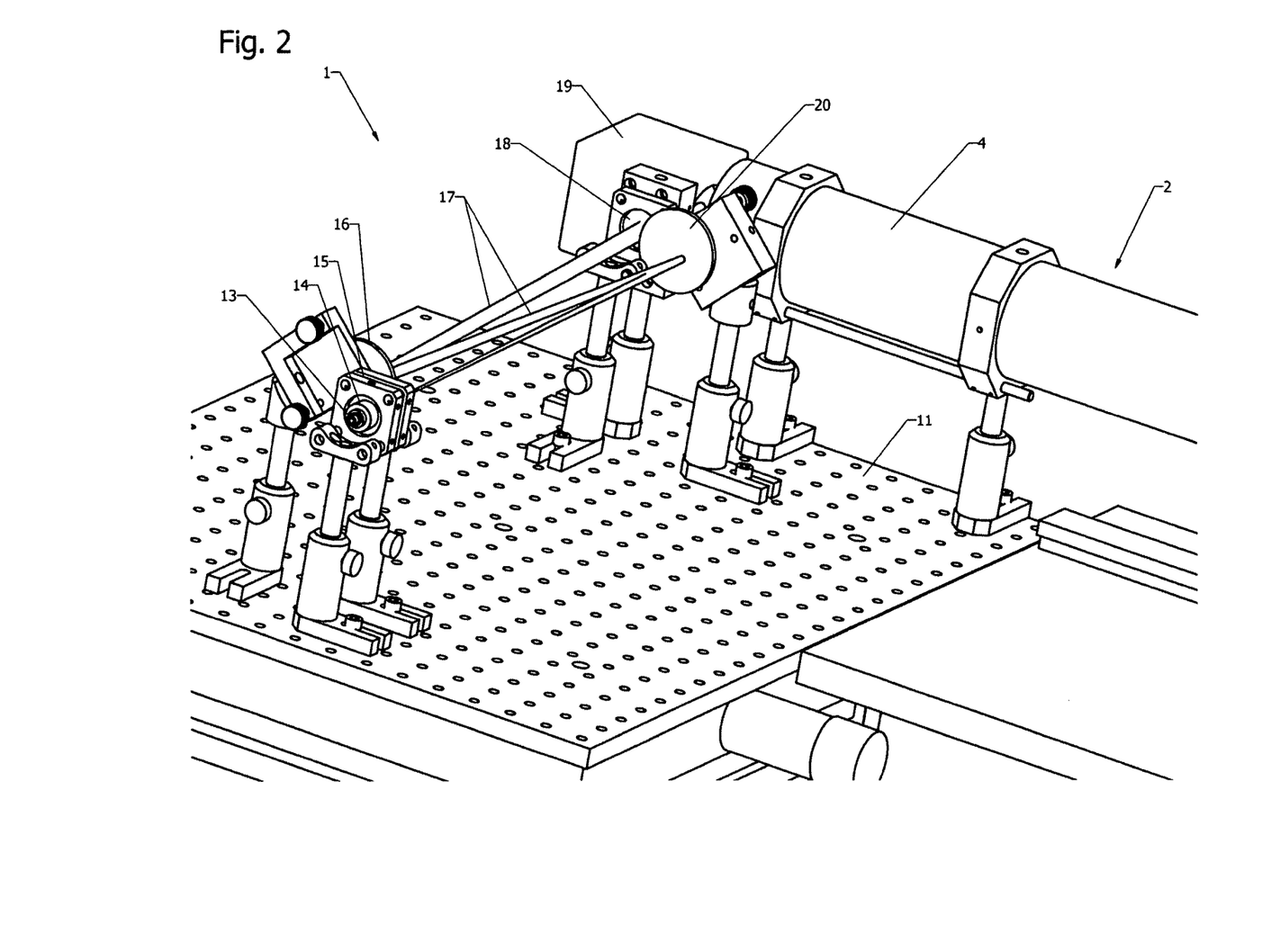
FIG. 2 shows schematically an enlarged view of the bread board part of the apparatus of FIG. 1, with a scan head as a scanning device.

The illumination part 1 is shown in more detail in FIG. 2. A laser beam is coupled into the system at a laser input 13. In the example shown, this is done by an aperture matched collimation lens 14 (note that other coupling mechanisms known to the expert in the field may be used as well). After the lens 14, a pinhole 15 is placed, which is mapped with an anti-reflectance coated spherical singlet lens 18 (with f=1000 mm) by a 2f image on the subject (sample). Before the beam 17 arrives at the lens 18, which is placed directly in front of a scan head 19, the light beam 17 is guided to a small optical resonator is made of two coated economy front surface mirrors 16, 20. The light travels the distance between the mirrors 16, 20 five times before reaching the scan head 19, where it is reflected by two galvanometric driven mirrors (contained within the scan head 19, not shown in detail) which allow the scanning of the sources (i.e. the scanning of the focal spot, compare FIG. 5, by moving these mirrors as optical elements) on the surface of the sample. These mirrors deflect the beam approximately by 90° from the input direction. The scan head 19 acts as the scanning device of the apparatus. The beam is then directed through a rigid linkage 2, which is here separated in the middle (compare FIG. 1, tubes 4, 5) to facilitate handling, to the sample platform placed in the magnet. All components located outside the magnet 9 are fixed on a home build breadboard 11, the position of which can be adjusted in the two orthogonal directions of the horizontal plane.

Figure 3:
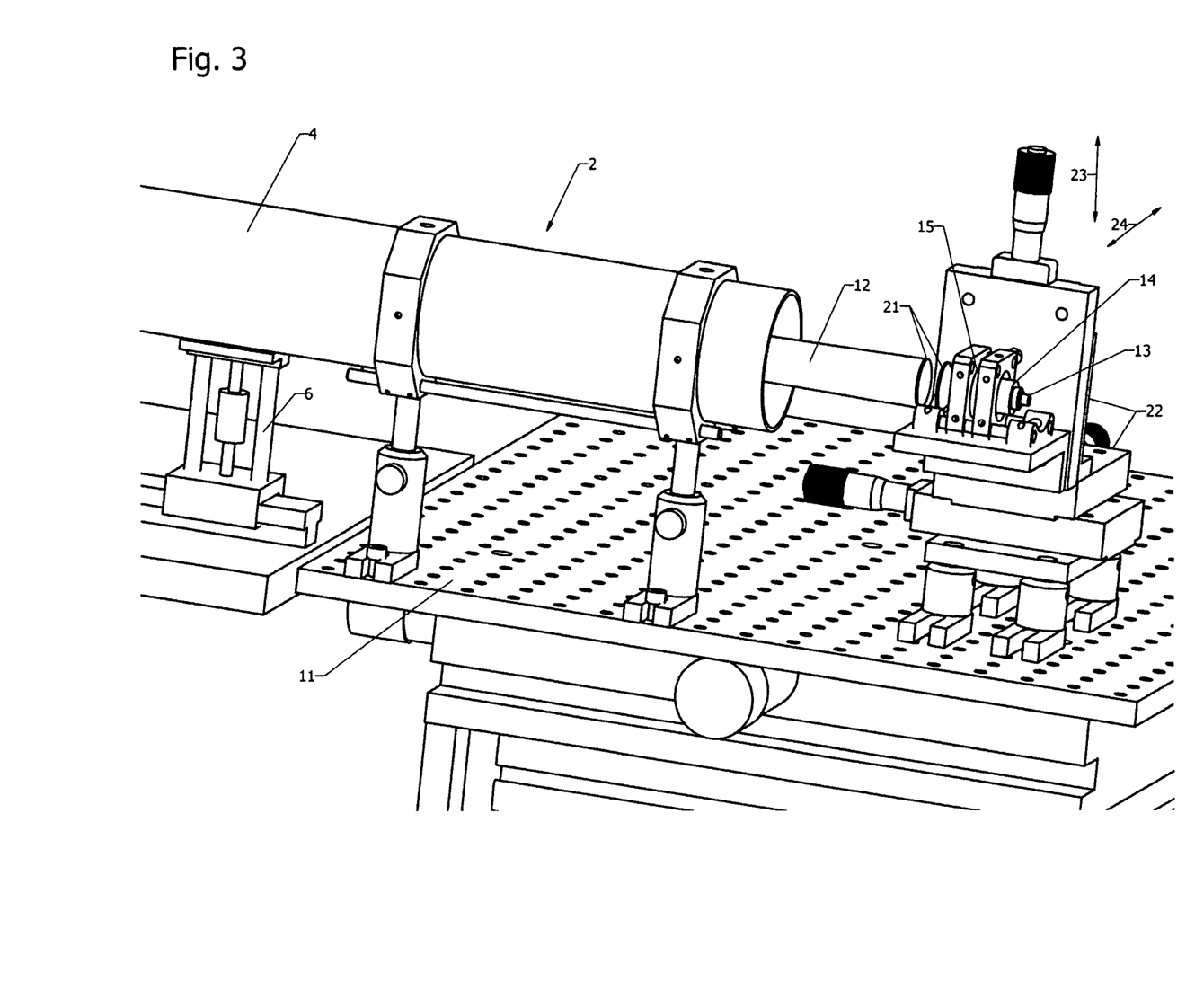
FIG. 3 shows schematically an alternative bread board part of an inventive apparatus, with a xy stage as a scanning device.

FIG. 3 illustrates a further way to scan the light beam (or its focal spot) outside the magnet bore in accordance with the invention, as an alternative to the scan head shown in FIG. 2. A motorized xy stage 22 is placed on the bread board 11. The xy stage 22 carries the laser input 13 (where the output end of a fiber transporting a laser beam from a laser is fixed, not shown) as well as the collimation lens 14, the pinhole 15 and a lens system 21 for focusing the laser beam 12. By moving the equipment carried by the xy stage 22, the laser beam 12 can be shifted in two directions 24, 25 radially relative to the axis of the rigid linkage 2, and thus relative to the sample (typically after a reflection by a mirror, as shown with ref. no. 26 in FIG. 4). By this means, the output end of the fiber at the laser input 13 can be imaged to and scanned on the sample surface by moving said output end.

Figure 4:
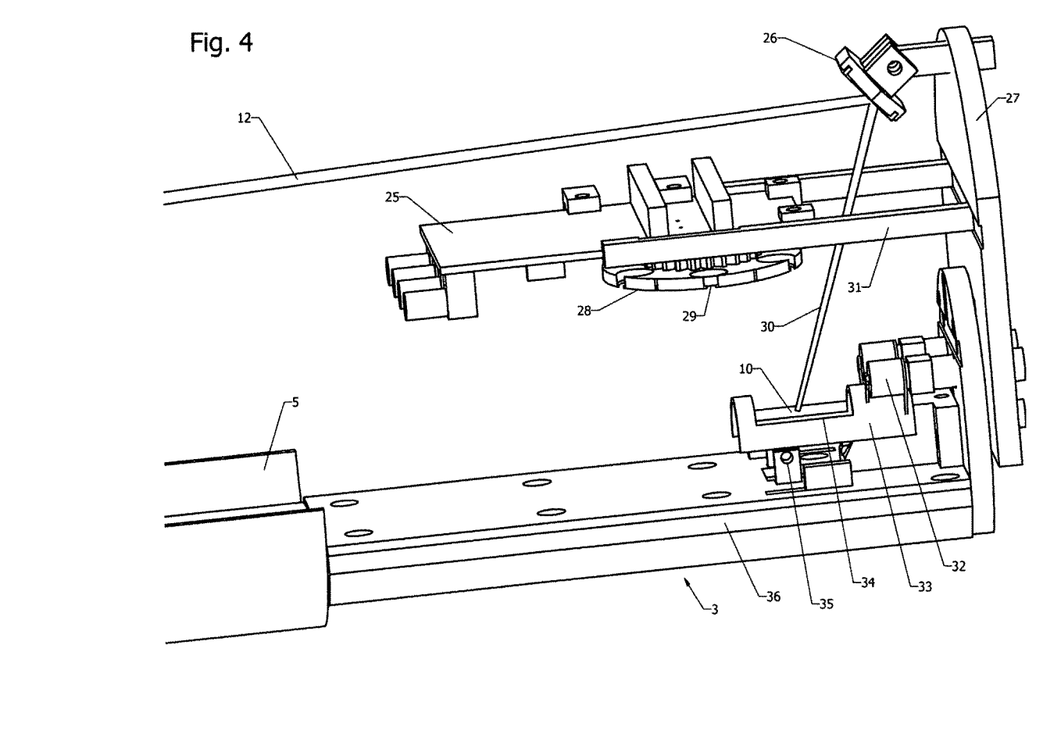
FIG. 4 shows schematically an enlarged view of the sample platform part of the apparatus of FIG. 1.

As shown in FIG. 4, at the end of the tube 5, the sample platform 3 is mounted. Attached to the sample platform 3 is a blackened rare flange 27, which is linked to a pcb holder 31 for the detector pcb 25 and linked to a deflection mirror 26 for deflection of the laser beam 12 to the sample position 10 (or, more exactly, to the surface of the object). The scan head is scanning arbitrary (grid) points on the sample within the camera field of view.

As an example, we show the sample platform 3 designed for head imaging. Analogous supports can be designed for imaging any body region of the animals or even for whole body imaging. The sample platform 3 comprises an animal/sample support 36 (where the body of the animal is located, note that the animal is not shown in FIG. 4), and a head support. The head support comprises a pair of integrated stereotactic ear bars for head fixation (compare stereotactic fixation 35). A tooth bar is fixed in the animal face mask, which was used for the administration of anesthesia gases (not shown). The sample platform 3 comprises a water heating, maintaining the animals on the animal support 36 at a constant temperature during the measurement.

A head adapted RF coil 33 with tuning and matching capacities (see trimmer capacitors 32) is positioned between the sample position 10 and the detector, compare detector pcb 25. The coil design is such that it allows the passage of exciting and fluorescent light through a coil opening (see window 34). The optical detector is here an array of single-photon avalanche diodes (SPAD) bonded on a printed circuit board (pcb) 25. A fixed focus low profile lens (not shown in FIG. 4, compare FIG. 5) is glued directly to the pcb 25 on the top of the detector array providing a field of view (FOV) at a fixed focal distance covering the head of the animal.

The light beam 12 from outside the magnet bore impinging on the small mirror 26 placed in the back wall (flange 27) of the animal/sample support 36 deflects the beam 12 to the surface of the sample at the sample position 10. The back-scattered light is filtered upon passage through a filter wheel 28 containing optical band pass filter elements 29 for different wavelength domains. The filter wheel 28 is positioned between the animal (sample) and the SPAD detector array.

For each laser illumination point, the light intensity distribution on the animal's surface is recorded. Imaging data sets are collected at the excitation wavelength and at various emission wavelengths. A small light emitting diode (LED) strip (not shown) mounted to the rear flange 27 of the animal/sample support 36 at the back wall is providing light for the white light illumination during the reference surface image acquirement. All the parts used for the animal/sample support 36 and the sample platform 3 are made from materials not interfering with high magnetic fields.

It should be noted that the means for directing the light beam shown in the figures are to be understood as examples only, and the expert in the field can use other equipment known to him without departing from the scope of the present invention.

The setup is fully computer controlled and the software allows an automatic acquirement of the image needed for tomographic reconstruction. Optical tomography is analog to X-ray computed tomography and uses multiple projections to generate the final image. Optical tomography requires a number of optical measurements from light-source/detector pairs through bulk tissue and an appropriate forward model to predict the light propagation within an optically diffusive media to finally solve an inverse problem to gain the fluorescence light distribution within the volume of interest.

Figure 5:
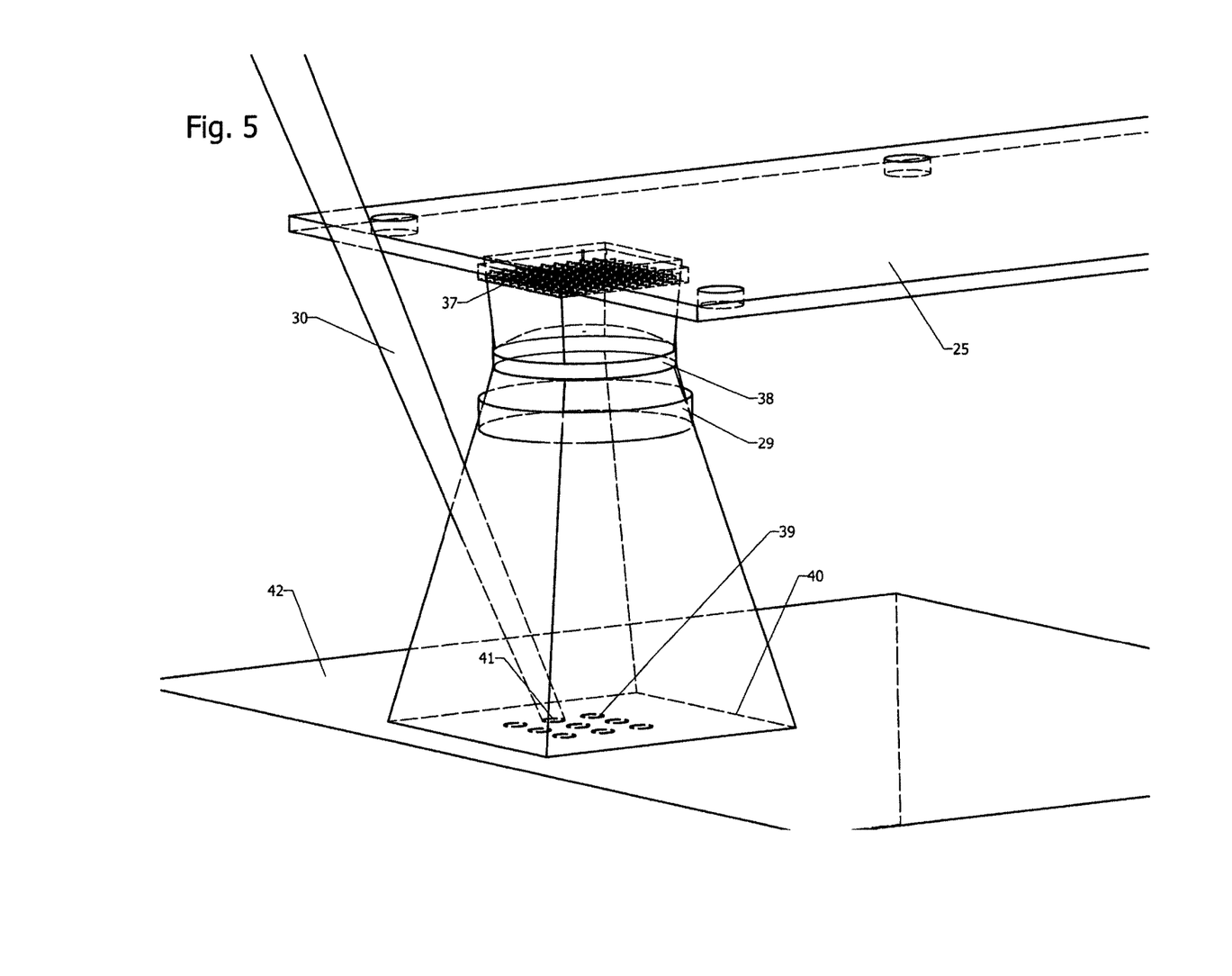
FIG. 5 shows schematically the optical imaging setup within the apparatus of FIG. 1.

As shown in FIG. 5, to measure the different source/detector pairs, the subject (sample 42) is placed in the field of view (FOV) 40 of the detector 37 (which here is an array of 32×32 one-element-detector elements, shown only schematically in FIG. 5), and the number and arrangement of sources on the subject is chosen and set through the software. A source is a focal spot 41 of the incoming deflected laser beam 30 on the sample 42. During the measurement, the focal spot 41 is scanned to different positions of a point scan grid 39 (in FIG. 5, a 3×3 grid is shown). For each position of the focal spot 41 on the point scan grid 39, the detector 37 records position sensitive images of the field of view 40 of the sample 42. The fluorescence light passes the filter element 29 and an objective lens 38 for this imaging. It should be noted that a typical field of view 40 has a size of 8 mm×8 mm, and a focal spot 41 has a typical diameter of 2 mm. The detector 37 is at a distance of about 20-30 mm to the sample. The distance of the detector 37 to the sample 42 is typically larger than the dimension (and preferably larger than two times the dimension) of its field of view 40 on the sample 42 so the beam 30 can be scanned properly.

In the following, an experiment performed by the inventors with the inventive apparatus is described.

Before data acquisition, two calibration measurements were performed: one to match the scan head coordinate system with the pixel coordinate system of the detector, and the other to find the pixel dimensions in centimeters. Then the scanning procedure was started and a fluorescence and excitation data set was acquired with the corresponding filters. The setup shown here was built to acquire in reflectance mode where the detector and the light source are placed at the same side of the subject. One image was recorded for each source position, resulting in an $N_x*N_y*N_S$ array of images, where $N_x$ and $N_y$ is the number of pixels in x and y direction and $N_S$ is the number of sources. At the end, a background image was acquired for each filter position without any laser irradiation. A white light image of the subject surface was acquired to localize the fiducial markers on the sample which were used later on to match optical and MRI data.

The light propagation in tissue for setting up the forward problem was modeled by a so-called diffusion approximation of the radiative transfer equation. The diffusion equation was solved for a slab geometry with extrapolated boundary conditions resulting in a system of linear equations.

Further, a normalized Born algorithm [14] was then applied on the linear equations to get the normalized Born intensities. This algorithm, based on the excitation measurement to account for the intrinsic tissue properties, cancels out the position dependent factors. After discretizing the volume of interest, a system of linear equations can be formulated in matrix form $y=W*x$, where y are the source-detector measurements now represented by the normalized Born intensities, x the fluorochrome concentration at each position in the generated mesh within the volume of interest, and W is the weight matrix describing the light propagation in tissue. In general, this problem is ill-posed and needs numerical techniques for inversion such as an algebraic reconstruction technique (ART). This iterative algorithm was used for fluorophore distribution reconstruction.

LIST OF REFERENCE SIGNS

1. Illumination part
2. Rigid linkage
3. Sample platform
4. Tempered glass tube
5. Tempered glass tube
6. Guiding
7. Stop
8. Room temperature bore
9. Magnet
10. Sample position at isocenter
11. Bread board
12. Laser beam sent to the sample
13. Laser input
14. Collimation lens
15. Pinhole
16. Resonator mirror 1
17. Laser beam in the resonator
18. Lens for beam focusing
19. Scan head
20. Resonator mirror 2
21. Lens system for beam focusing
22. Motorized xy-stage for scanning
23. Scan direction
24. Scan direction
25. Detector pcb
26. Deflection mirror
27. Rare flange
28. Filter wheel
29. Filter element
30. Deflected laser beam
31. Pcb holder
32. Trimmer capacitors
33. RF coil
34. Window
35. Stereotactic fixation
36. Animal/sample support
37. Detector
38. Objective lens
39. Point scan grid
40. Field of view
41. Focal spot
42. Sample

REFERENCES

[1] Ciprian Catana, Yibao Wu, Martin S. Judenhofer, Jinyi Qi, Bernd J. Pichler, and Simon R. Cherry. Simultaneous acquisition of multislice PET and MR images: Initial results with MR-compatible PET scanner. The Journal of Nuclear Medicine, 47(12):1968-1976, December 2006.

[2] Bernd J. Pichler, Martin S. Judenhofer, Ciprian Catana, Jeffrey H. Walton, Manfred Kneilling, Robert E. Nutt, Stefan B. Siegel, Claus D. Claussen, and Simon R. Cherry. Performance test of an LSO-APD detector in a 7-T MRI scanner for simultaneous PET/MRI. Journal of Nuclear Medicine, 47:639-647, 2005.

[3] Edward E. Graves, Jorge Ripoll, Ralph Weissleder, and Vasilis Ntziachristos. A submilimeter resolution fluorescence molecular imaging system for small animal imaging. Medical Physics, 30(5):901-911, May 2003.

[4] Vasilis Ntziachristos, Eyk A. Schellenberger, Jorge Ripoll, Doreen Yessayan, Edward Graves, Alexei Bogdanov, Lee Josephson, and Ralph Weissleder. Visualization of antitumor treatment by means of fluorescence molecular tomography with an annexinV-Cy5.5 conjugate. PNAS, 101(33):12294-12299, August 2004.

[5] Murat Guven, Birsen Yazici, Xavier Intes, and Britton Chance. Diffuse optical tomography with a priori anatomical information. Physics in Medicine and Biology, 50:2837-2857, February 2005.

[6] Fluorescence optical tomography with a priori information, volume 6431. SPIE, 2007.

[7] Damon Hyde, Ruben DeKleine, Sarah A. MacLaurin, Eric Miller, Dana H. Brooks, Thomas Krucker, and Vasilis Ntziachristos. Hybrid FMT-CT imaging of amyloid-_plaques in a murine Alzheimer's disease model. Neuroimage, 1:8-9, 2008.

[8] Elucidating Structure and Function In Vivo With Hybrid Fluorescence and Magnetic Resonance Imaging, volume 96. IEEE, March 2008.

[9] Mathieu Allard, Daniel C^ot e, Lorinda Davidson, Jun Dazai, and R. Mark Henkelman. Combined magnetic resonance and bioluminescence imaging of live mice. Journal of Biomedical Optics, 12(3):034018-1-034018-11, May/June 2007.

[10] Sean Merritt, Frederic Bevilacqua, Anthony J. Durkin, David J. Cuccia, Ryan Lanning, Bruce J. Tromberg, Gultekin Gulsen, Hon Yu, Jun Wang, and Orhan Nalcioglu. Coregistration of diffuse optical spectroscopy and magnetic resonance imaging in a rat tumor model. Applied Optics, 42(16):2951-2959, June 2003.

[11] David J. Cuccia, Frederic Bevilacqua, Anthony J. Durkin, Sean Merritt, Bruce J. Tromberg, Gultekin Gulsen, Hon Yu, Jun Wang, and Orhan Nalcioglu. In vivo quantification of optical contrast agent dynamics in rat tumors by use of optical spectroscopy with magnetic resonance imaging coregistration. Applied Optics, 42(16):2940-2950, June 2003.

[12] Heng Xu, Roger Springet, Hamid Dehghani, Brian W. Pogue, Keith D. Paulsen, and Jeff F. Dunn. Magentic-resonance-imaging-coupled broadband near-infrared tomography system for small animal brain studies. Applied Optics, 44(11):2177-2188, April 2005.

[13] Britton Chance, Robert F. Alfano, Bruce J. Tromberg, Mamoru Tamaura, and Eva M. Sevick-Muaraca, editors. Combined optical tomography and magnetic resonance imaging of tumor bearing mice, volume 5693 of Optical Tomography and Spectroscopy of Tissue VI. SPIE, 2005.

[14] Vasilis Ntziachristos and Ralph Weissleder. Experimental three-dimensional fluorescence reconstruction of diffuse media by use of a normalized born approximation. Optics Letters, 26(12):893-895, June 2001.

We claim:

1. A dual modality imaging apparatus for investigating a sample located at a sample position, the apparatus comprising:
a magnetic resonance imaging (=MRI) system, said magnetic resonance imaging system having a magnet with a room temperature bore within which the sample position is located, said room temperature bore having a longitudinal axis, said magnetic resonance imaging system further comprising a radio frequency coil having at least one window, said at least one window opening in a transverse direction, substantially perpendicular to said longitudinal axis of said room temperature bore, wherein said radio frequency coil is disposed within said room temperature bore and the sample is at least partially within said coil; and
a fluorescence molecular tomography (=FMT) system having a mechanism for directing a light beam towards the sample position and a position-sensitive detector, said position-sensitive detector having electrical connections, said position-sensitive detector and said electrical connections being disposed within said bore and outside said radio frequency coil to detect fluorescence light from the sample, wherein at least part of the sample is imaged onto said position-sensitive detector, said mechanism for directing said light beam having a focusing device for focusing said light beam into a focal spot on the sample, a scanning device structured for continuously scanning said focal spot on the sample and a deflection mirror, said scanning device being disposed outside of said room temperature bore and said deflection mirror being disposed inside said room temperature bore, wherein said mechanism for directing said light beam, said radio frequency coil and said position-sensitive detector are disposed, structured and dimensioned such that said light beam enters said room temperature bore substantially parallel to said longitudinal axis and is deflected by said deflection mirror in a substantially transverse direction to pass through said at least one window of said radio frequency coil and illuminate the sample, wherein fluorescence light emanating from the sample passes through said at least one window in said radio frequency coil and is incident on said position sensitive detector, the apparatus thereby being adapted for simultaneous measurement of MRI data and FMT data.

2. The apparatus of claim 1, wherein said FMT system comprises a rigid linkage connecting said scanning device with a sample platform for supporting the sample at the sample position.

3. The apparatus of claim 2, wherein said FMT system comprises a guiding and/or a stop located within said bore for inserting and positioning said rigid linkage.

4. The apparatus of claim 1, wherein said scanning device is adapted to move an optical element into different positions corresponding to different positions of said focal spot of said light beam on the sample, wherein said optical element directs said light beam.

5. The apparatus of claim 4, wherein said optical element reflects or guides said light beam.

6. The apparatus of claim 4, wherein said scanning device comprises at least one of a scanhead, one or more galvanometric driven mirrors, and an xy stage carrying an optical fiber guiding said light beam, wherein a fiber output of said optical fiber is imaged on the sample.

7. The apparatus of claim 1, wherein said FMT system has a pinhole which is imaged onto the sample by said focusing device via said scanning device to form said focal spot.

8. The apparatus of claim 7, wherein said focusing device comprises a lens with a focal length of f, and an optical distance of said pinhole and said lens as well as an optical distance of said lens and said focal spot on the sample is 2*f.

9. The apparatus of claim 1, wherein said scanning device is arranged for scanning said focal spot on a side of the sample facing said position sensitive detector (=reflection mode arrangement) or said scanning device is arranged for scanning said focal spot on a side of the sample opposite said position sensitive detector (=transmission mode arrangement).

10. The apparatus of claim 1, wherein said FMT system comprises a plurality of mirrors between a source for said light beam and said scanning device.

11. The apparatus of claim 1, wherein said RF coil is a surface coil, a saddle coil, a bird cage resonator or an Alderman-Grant resonator.

12. The apparatus of claim 1, wherein said FMT system comprises a filter device located in front of said position-sensitive detector.

13. The apparatus of claim 12, wherein said filter device comprises a plurality of selectable or interchangeable filter elements or a plurality of filter elements disposed on a filter wheel.

14. The apparatus of claim 1, wherein said position-sensitive detector is an array detector, a Single Photon Avalanche Diode (=SPAD) array, a Charge Coupled Device (=CCD) array or a CMOS array.

15. Use of the apparatus of claim 1 to simultaneously record MRI data and FMT data.

* * * * *